(12) United States Patent
Roady

(10) Patent No.: US 8,423,377 B2
(45) Date of Patent: Apr. 16, 2013

(54) MEDICAL CASE SCHEDULING, LOGISTICS MANAGEMENT AND ASSOCIATED DATA MANAGEMENT

(76) Inventor: Mark Roady, Scottsdale, AZ (US)

(*) Notice: Subject to any disclaimer, the term of this patent is extended or adjusted under 35 U.S.C. 154(b) by 1183 days.

(21) Appl. No.: 11/639,392

(22) Filed: Dec. 13, 2006

(65) Prior Publication Data

US 2007/0185733 A1    Aug. 9, 2007

Related U.S. Application Data

(60) Provisional application No. 60/750,148, filed on Dec. 13, 2005.

(51) Int. Cl.
*G06Q 10/00* (2012.01)
*G06Q 50/00* (2012.01)

(52) U.S. Cl.
USPC ................................. 705/2; 705/3; 705/7.16

(58) Field of Classification Search .................. 705/1–3, 705/8, 7; 709/204
See application file for complete search history.

(56) References Cited

U.S. PATENT DOCUMENTS

| 5,842,173 | A | * | 11/1998 | Strum et al. | 705/1 |
| 6,389,454 | B1 | * | 5/2002 | Ralston et al. | 709/204 |
| 2002/0077849 | A1 | * | 6/2002 | Baruch et al. | 705/2 |
| 2006/0143060 | A1 | * | 6/2006 | Conry et al. | 705/8 |

* cited by examiner

*Primary Examiner* — Joseph Burgess
(74) *Attorney, Agent, or Firm* — Luis M. Ortiz; Kermit D. Lopez; Melissa Silverstein

(57) ABSTRACT

Methods and systems enable the electronic scheduling of medical procedures. Schedulers log into a scheduling system to electronically submit medical procedure requests. Requests include entry of patient data together with at least one of: procedure date, procedure place, procedure time, required equipment, requested medical personnel, as part of the first medical procedure request. Once request is accepted by the scheduling system, electronic notifications about the request are automatically sent over a data network to parties associated with the medical procedure (e.g., medical facility, medical personnel, equipment distributors). System enables rescheduling or resolution where scheduling conflicts are indicated.

16 Claims, 17 Drawing Sheets

FIG. 7

WELCOME

PLEASE SIGN IN   Barb

PATIENT INFORMATION

Today's Date: 11/30/05  Scheduler: Barb  Office Phone Number: 602-406-8844

Patient Last Name: Doe  Patient First Name: John

Patient's Address: 123 E. Main Street  Primary laungage: _____
(If not English)

City: Phoenix

State: AZ  Zip: 85034  SSN: 123-45-6789

Sex: Male  Age: 45  DOB: 03/20/1960

Phone Number: 602-456-1793  Work: 602-456-1919  (CELL): 480-769-8282

CODING

Diagnosis: Scoliosis; degenerative  ICD-9 Codes: 737.39  Procedure: Scoliosis  CPT Codes: 913746

Levels (If applicable): T4-L2

Approach Surgeon: Mike Edwards, M.D.

1st Assist: Jeff Harris, M.D.  2nd Assist: Bob Long, M.D.

INSURANCE

Type: PPO

Industrial Company Name: _____  Phone No: _____

Attorney/Adjuster: _____  Phone No: _____

Employer: _____  DOI: _____  Claim No: _____

Primary Insurance Co: Blue Cross Blue Shield  Policy No: JD979758

Effective Date: 01/01/2001  Phone No: 602-246-3000

Insurance Benefits Verified with: Tammy  Date: 11/30/2005

Pre-Authorization Phone No. 602-246-3461  Pre-Authorization No. BCBS11302005

Secondary Insurance Co: United Health Insurance  Policy No: UHI6428

Effective Date: 07/01/2004  Phone No: 505-888-9000

Insurance Benefits Verified with: Julie  Date: 11/30/05

Pre-Authorization Phone No. 505-888-9000  Pre-Authorization No. JH54LM442

Private room: Patient Request

SCHEDULING

FIG 9

| | | | |
|---|---|---|---|
| Surgeon: | William Stevens, M.D. | Hospital: | Desert Samaritan Hospital |
| Surgery Date: | 12/07/05 | Surgery Start time: 7:30 AM | OR Time Needed: 4 hours | Block time: YES |

Hosptial Equipment Required: C-Arm, Microscope, Power Tools    Table Required: Regular OR Table

Anesthesia: Bill Tohner, M.D.    Type: General

Monitoring: Best Monitoring    Type: Video, SSEP/EMG, BAEP

Profusion: Cell Saver

Equipment: YES    Bracing: YES

Orders (Pre-op): CBC, Chest X-ray, Urine, EKG

Autologous Blood: YES    Send to Blood Bank: Desert Labs    Units: 1 to 2

RX: Sent/Given to patient: YES    Consent Forms (Surgery): YES

Primary Care Physician:

PCP: Dr. James Daily    Phone No: 815-432-5000    Fax No: 815-432-5500

Hospital information:

Admission Date: 12/06/05    Admission Time: 2:00 PM    Length of Hospital Stay: 4 days If admitting day before surgery, please specify reason: _____

Does authorization include day before surgery admission: ____

Positioning: Prone

Patient informed on: 11/30/05    Packet sent on: 12/01/05

FIG 10

PLEASE CHOOSE PRODUCTS FOR CASE

☒ CHECK ALL THAT APPLY:

☒ DePuy     ☐ Danek     ☐ Synthes     ☐ Stryker

☐ Abott Spine     ☒ LifeNet     ☐ Enduis     ☐ EBI

☒ Brace--Please Select    Hanger

☐ Bone Growth Stimulators: Int/Ext Co:_____

◀◀◀ BACK                    SUBMIT ▶▶▶

FIG 11

**PLEASE COMPLETE ALL CATEGORIES
AND THEN HIT THE ARROW**

BRING TO CASE | DePuy (MAR Medical)

CAGES | Devex—DePuy—MAR Medical

ANTERIOR CERVICAL | N/A

LUMBAR & THORACIC | Moss Miami SI—DePuy—MAR Medical

MINIMALLY INVASIVE | N/A

OSTEOBIOLOGICS | I/C Graft Chambers—LifeNet—MAR Medical

LIFENET | N/A

BRACE | Lumbar Classic III—Hanger—MAR Medical

◄◄◄ BACK

SUBMIT YOUR ORDER BELOW

SUBMIT ►►►

FIG 12

THE FOLLOWING IS A LIST OF PEOPLE WHO WILL BE NOTIFIED OF THE CASE

PLEASE VERIFY BEFORE SUBMITTING

| | |
|---|---|
| Patient | John                Doe |
| Primary Insurance | Blue Cross Blue Shield |
| Secondary Insurance | United Health Insurance |
| Surgeon | William Stevens, M.D. |
| Hospital | Desert Samaritan Hospital |
| Anesthesia | Bill Tonner, M.D. |
| Monitoring | Best Monitoring |
| Med-Advise Consulting | James Bond |
| Cell Number: | 602-007-0007 |

YOUR MED-ADVISE CONSULTANT WILL CONTACT THE FOLLOWING DISTRIBUTORS TO BRING YOUR REQUESTED PRODUCTS

| | |
|---|---|
| CAGES | Devex--DePuy--MAR Medical |
| ANTERIOR CERVICAL | N/A |
| LUMBAR & THORACIC | Moss Miami SI--DePuy--MAR Medical |
| MINIMALLY INVASIVE | N/A |
| OSTEOBIOLOGICS | I/C Graft Chambers--LifeNet--MAR Medical |
| LIFE NET | N/A |
| BRACE | Lumbar Classic III--Hanger--MAR Medical |

SUBMIT YOUR ORDER BELOW

◄◄◄ *BACK*          *CASE CONNECT*

FIG. 13

FROM THE OFFICE OF WILLIAM STEVENS, M.D.

| | | | | | |
|---|---|---|---|---|---|
| Date Prepared: | 11/30/05 | | Scheduler: | Barb | Office Phone: 602-406-8844 |

Patient: John Doe
Phone Number:
Address: 123 E. Main Street    Home: 602-456-1793
Phoenix  AZ    Work: 602-456-1919
85034    Cell: 480-769-8282

Sex: Male    Age: 45    DOB: 03/20/1960

Diagnosis: Scoliosis, degenerative    ICD-9 Codes: 737.39
Procedure: Scoliosis    CPT Codes: 913746
Levels (if applicable): T4-L2

Primary Insurance: Blue Cross Blue Shield    ID# JD979758
Effective date: 01/01/2001    Phone Number: 602-246-3000
Pre-Athorization Number: BCBS11302005

Secondary Insurance: United Health Insurance    ID# UHI6428
Effective date: 07/01/2004    Phone Number: 505-888-9000
Pre-Athorization Number: JH54LM442

Surgon: William Stevens, M.D.    Hospital: Desert Samaritan Hospital
DOS: 12/07/05    Start time: 7:30 AM    OR Duration: 4 hours
Approach Surgeon: Mike Edwards, M.D.
1st Assist: Jeff Harris, M.D.    2nd Assist: Bob Long, M.D.
Anesthesia: Bill Tonner, M.D.    Type: General Hospital Equipment
Required: C-Arm, Microscope, Power Tools    Monitoring: Best Monitoring
    Type: Video, SSEP/EMG, BAEP Table Required: Regular OR Table    Profusion: Cell Saver Pre-Op Orders: CBC, Chest X-ray, Urine, EKG    Blood Work: Desert Labs
    Units: 1 to 2

Positioning: Prone

Equipment:    Med-Advise Consultant: James Bond
  CAGES    Devex--DePuy--MAR Medical    Cell Number: 602-007-0007
  ANTERIOR CERVICAL    N/A
  LUMBAR & THORACIC    Moss Miami SI--DePuy--MAR Medical
  MINIMALLY INVASIVE    N/A
  OSTEOBIOLOGICS    I/C Graft Chambers--LifeNet--MAR Medical
  LIFE NET    N/A
  BRACE    Lumbar Classic III--Hanger--MAR Medical PCP: Dr. James Daily
Office: 815-432-5000
Fax: 815-432-5500

FIG 14

Notification of Scheduled Case

| | | |
|---|---|---|
| Surgeon: | William Stevens, M.D. | Consultant: James Bond |
| | | Cell Number: 602-007-0007 |
| Date: | 12/07/2005 | |
| Time: | 7:30 AM | |
| Hospital: | Desert Samaritan Hospital | |
| Procedure: | Scoliosis | Levels: T4-L2 |
| | | (If applicaable) |

Instrumentation Requested:

| | |
|---|---|
| CAGES | Devex--DePuy--MAR Medical |
| ANTERIOR CERVICAL | N/A |
| LUMBAR & THORACIC | Moss Miami SI--DePuy--MAR Medical |
| MINIMALLY INVASIVE | N/A |
| OSTEOBIOLOGICS | I/C Graft Chambers--LifeNet--MAR Medical |
| LIFE NET | N/A |
| BRACE | Lumbar Classic III--Hanger--MAR Medical |

Patient Name:   John   Doe

Patient Age:   45

FIG 15

Notification of Scheduled Case at
Desert Samaritan Hospital

| | | | | | |
|---|---|---|---|---|---|
| Date: | 12/07/2005 | Surgeon: | William Stevens, M.D. | | |
| Time: | 7:30 AM | Approach Surgeon: | Mike Edwards, M.D. | | |
| Block: | YES | 1st Assist: Jeff Harris, M.D. | | 2nd Assist: | Bob Long, M.D. |
| Diagnosis: | Scoliosis, degenerative | ICD-9 Codes: | 737.39 | | |
| Procedure: | Scoliosis | Levels: T4-L2 (if applicable) | | CPT Codes: | 913746 |

Hospital Equipment Required: C-Arm, Microscope, Power Tools         Positioning: Prone
Table Required: Regular OR Table Anesthesia: Bill Tonner, M.D.                    Type: General Monitoring: Best Monitoring                      Type: Best Monitoring Profusion: Cell Saver Instrumentation Requested will be Coordinated by MED-ADVISE CONSULTING

PRODUCTS REQUESTED:

Consultant: James Bond

Cell Number: 602-007-0007

| | |
|---|---|
| CAGES | Devex--DePuy--MAR Medical |
| ANTERIOR CERVICAL | N/A |
| LUMBAR & THORACIC | Moss Miami SI--DePuy--MAR Medical |
| MINIMALLY INVASIVE | N/A |
| OSTEOBIOLOGICS | I/C Graft Chambers--LifeNet--MAR Medical |
| LIFE NET | N/A |

Orders (pre-op): CBC, Chest X-ray, Urine, EKG

Blood work: Desert Labs                  Units: 1 to 2

Patient Name: John    Doe                        DOB: 03/20/1960

Patient Address: 123 E. Main Street              Age: 45
                 Phoenix    AZ    85034
                                                 SSN: 123-45-6789
Phone Numbers:
    Home: 602-456-1793
    Work: 602-456-1919
    Cell: 480-769-8282

Insurance: (primary)    Blue Cross Blue Shield    Policy No: JD979758
Phone:          602-246-3000                      Effective date: 01/01/2001
Pre-Authorization No.   BCBS11302005

Insurance: (secondary)  United Health Insurance   Policy No: UHI6428
Phone:          505-888-9000                      Effective date: 07/01/2004

Admit Date: 12/06/2005       Time: 2:00 PM        Private Room: Patient Request

FIG 16

Notification of scheduled case for Monitoring

| | | | |
|---|---|---|---|
| Monitoring: | Best Monitoring | Type: | Best Monitoring |
| Date: | 12/07/2005 | Hospital: | Desert Samaritan Hospital |
| Surgeon: | William Stevens, M.D. | | |
| Time: | 7:30 AM | | |
| Block: | YES | | |
| Diagnosis: | Scoliosis, degenerative | ICD-9 Codes: | 737.39 |
| Procedure: | Scoliosis    Levels: T4-L2 (If applicable) | | CPT Codes: 913746 |
| Hospital Equipment Required: | C-Arm, Microscope, Power Tools | Positioning: | Prone |
| Table Required: | Regular OR Table | | |
| Anesthesia: | Bill Tonner, M.D. | Type: | General |
| Profusion: | Cell Saver | | |
| Patient Name: | John    Doe | | DOB: 03/20/1960 |
| Primary Insurance: | Blue Cross Blue Shield | Policy No: | JD979758 |
| Phone No: | 602-246-3000 | Effective Date: | 01/01/2001 |
| Pre-Authorization No: | BCBS11302005 | | |
| Secondary Insurance: | United Health Insurance | Policy No: | UHI6428 |
| Phone No: | 505-888-9000 | Effective Date: | 07/01/2004 |
| Pre-Authorization No: | JH54LM442 | | |

FIG 17

Notification of scheduled case for Anesethesia

| | | | |
|---|---|---|---|
| Anesthesia: | Bill Tonner, M.D. | Type: | General |
| Date: | 12/07/2005 | Hospital: | Desert Samaritan Hospital |
| Surgeon: | William Stevens, M.D. | Approach Surgeon: | Mike Edwards, M.D. |
| Time: | 7:30 AM | 1st Assist: | Jeff Harris, M.D. |
| Block: | YES | 2nd Assist: | Bob Long, M.D. |
| Diagnosis: | Scoliosis, degenerative | ICD-9 Codes: | 737.39 |
| Procedure: | Scoliosis | Levels: T4-L2 (If applicable) | CPT Codes: 913746 |

| | | | |
|---|---|---|---|
| Hospital Equipment Required: | C-Arm, Microscope, Power Tools | Positioning: | Prone |
| Table Required: | Regular OR Table | | |
| Monitoring: | Best Monitoring | Type: | Video, SSEP/EMG, BAEP |
| Profusion: | Cell Saver | | |
| Patient Name: | John    Doe | | DOB: 03/20/1960 |
| Primary Insurance: | Blue Cross Blue Shield | Policy No: | JD979758 |
| Phone No: | 602-246-3000 | Effective Date: | 01/01/2001 |
| Pre-Authorization No: | BCBS11302005 | | |
| Secondary Insurance: | United Health Insurance | Policy No: | UHI6428 |
| Phone No: | 505-888-9000 | Effective Date: | 07/01/2004 |
| Pre-Authorization No: | JH54LM442 | | |

FIG 18

Notification for Bracing

| | | | |
|---|---|---|---|
| Bracing Company: | Hanger | Type of Brace: | Lumbar Classic III–Hanger–MAR Medical |
| Surgery Date: | 12/07/2005 | Surgeon: | William Stevens, M.D. |
| Diagnosis: | Scoliosis, degenerative | ICD-9 Codes: | 737.39 |
| Procedure: | Scoliosis | Levels: T4-L2 (If applicable) | CPT Codes: 913746 |

Instrumentation Requested will be Coordinated by MED-ADVISE CONSULTING
Consultant: James Bond       Phone Number: 602-007-0007

Patient Name: John Doe

Patient Address: 123 E. Main Street
Phoenix   AZ   85034

Phone Numbers:
Home: 602-456-1793       DOB: 03/20/1960
Work: 602-456-1919       Age: 45
Cell: 480-769-8282       SSN: 123-45-6789

| | | | |
|---|---|---|---|
| Insurance: (primary) | Blue Cross Blue Shield | Policy No: | JD979758 |
| Phone: | 602-246-3000 | Effective date: | 01/01/2001 |
| Pre-Authorization No. | 602-246-3461 | | |
| Insurance: (secondary) | United Health Insurance | Policy No: | UHI6428 |
| Phone: | 505-888-9000 | Effective date: | 07/01/2004 |
| Pre-Authorization No. | JH54LM442 | | |

REQUEST FOR ORTHOSIS

Is the patient receiving this orthosis before surgery as:

☐ PreOp Stabilization          ☐ Reduce Pain
☐ Diagnostic Tool              ☐ Post-Op Stabilization Length of time needed: ☐
      ☐ As needed for specific activies
         Activity:_____
      ☐ Indefinitely
      ☐ Weeks          ☐ Months Describe Necessity:_____

FIG 19

Notification of scheduled case

| | | | |
|---|---|---|---|
| Patient: | John Doe | Surgeon: | William Stevens, M.D. |
| Arrive at hospital on: | 12/06/2005 | Time: | 2:00 PM |
| Hospital: | Desert Samaritan Hospital | Length of hospital stay: | 4 days |
| Hospital Address: | 1400 S. Dobson Road, Mesa, AZ  85789 | | |
| Hospital Phone Number: | 602-206-2000 | | |
| Surgery Date: | 12/07/2005 | Time of surgery: | 7:30 AM |

PRIOR TO SURGERY, PLEASE HAVE THE FOLLOWING TESTS COMPLETED:

| | | | |
|---|---|---|---|
| Orders (pre-op): | CBC, Chest X-ray, Urine, EKG | | |
| Blood work: | Desert Labs | Units: | 1 to 2 |
| Address: | 123 Arrowhead Ave., Phoenix, AZ  85224 | | |
| Phone: | 602-555-5555 | | |

PLEASE REMEMBER THAT YOU CAN NOT EAT OR DRINK ANYTHING AFTER MIDNIGHT
THE NIGHT BEFORE YOUR SURGERY (INCLUDING GUM, CANDY, OR WATER).

WEAR LOOSE OR COMFORABLE CLOTHING.

SOMEONE WILL NEED TO DRIVE YOU HOME FROM THE HOSPITAL.
YOU WILL NOT BE RELEASED WITHOUT A DRIVER.

IF YOU WERE FITTED FOR A BRACE AND HAVE IT WITH YOU ,
PLEASE BRING IT WITH YOU TO THE SURGERY.

IF YOU HAVE ANY QUESTIONS REGARDING YOUR SURGERY,
PLEASE FEEL FREE TO CONACT OUR OFFICT AT 602-406-8844

MEDICAL CASE SCHEDULING, LOGISTICS MANAGEMENT AND ASSOCIATED DATA MANAGEMENT

CONTINUING APPLICATION INFORMATION

The present invention claims priority to Provisional Application No. 60/750,148, filed Dec. 13, 2005, entitled "Medical Case Scheduling, Logistics Management, and Associated Data Management."

TECHNICAL FIELD

The present invention is related to automated data management solutions for use over data networks. More particular, the present invention is related to automated medical case scheduling, logistics management and associated data management. The systems described herein can be used by or on behalf of surgeons, medical facilities and third party suppliers of services and equipment.

BACKGROUND

Surgical case scheduling mishaps are commonplace in the medical field. Surgeons become increasingly frustrated with current processes that can be used to make sure they have proper logistics (e.g., instrumentation, facilities and personnel) available for their surgeries. Those serving the medical profession are also frustrated with current processes. For example, medical equipment distributors can deliver everything necessary for a procedure to the hospital only to find out the case had cancelled or moved. Worse, a distributor may get called from the operating room by a surgeon wondering where the equipment is (e.g., why implants were not delivered or made sterile). Late delivered equipment may have to be sterilized in the autoclave, which is not the optimal way to sterilize implants.

Medical case scheduling and planning can result in error because so many people are involved in the process. Surgeons, medical assistants, hospital staff, medical distributors, supporting specialists (e.g., anesthesiologists) must all be involved in the process prior to a scheduled operation. If one component in the process errs, the scheduled surgery may have to be cancelled, resulting with angry patients, surgeons, distributors, facilities and support staff. It may be caused by as simple a problem as a medical assistant forgetting to call the medical distributor to place an order for necessary parts (e.g., artificial joints). Such errors cause medical professionals and distributors unnecessary stress and potential liability from disgruntled or harmed patients. Surgeons and their patients are put at risk because the patient may have to endure more OR time, be administered more anesthesia and can suffer increased blood loss while the surgeon is waiting for equipment to arrive or other logistics to become available. Distributors may face the loss of business if a competitor must be called to provide an implant necessary to complete the scheduled case. Some loss of goodwill between the surgeon and losing distributor is inevitable no matter who was at fault.

Steps of medical scheduling and the distribution of medical devices currently occur as follows: The surgery scheduler verifies patient insurance coverage. If coverage is verified, typically 5 to 7 (or more) people will need to be notified of a scheduled case, including: the hospital, support personnel, monitoring personnel, equipment vendors and others. Scheduling is typically accomplished via telephone calls and faxes; although it can be appreciated that email communication can also be used. Unanswered phone calls or communications have to be returned by the scheduler.

Scheduling with so many parties involved is inefficient, inconsistent and can lead to errors. Hospitals are prone to errors because so many facets of a case are handled at the operating facility. Hospital staff must schedule a time for the operation, which can include coordinating the schedule for necessary personnel (e.g., anesthesiologists). On the day of surgery, hospital staff must verify/secure equipment delivery, sterilize instruments and implants (if applicable) and notify surgeon if equipment is not delivered or is late.

Medical device distributors are also prone to errors that may affect a scheduled case where the product is not shipped timely from the manufacturer, is mis-ordered, or the shipment is affected by resources outside of their control (e.g., transport carrier delays, bad weather). Inventory availability can affect shipment because product is shared within whole distributor systems (including several states) and inventory may be inadequate for coverage of the serviced market.

Much frustration and risk is experienced with faulty surgery scheduling. Many collateral issues also impact the scheduling process. For example: Merging companies are creating confusion with the surgeons and hospitals. Distributors and Sales Reps are losing product lines as a result of company mergers, acquisitions and sales. Manufacturers constantly change commission rate structures. Sales Reps territories keep getting cut. Scheduling conflicts are felt throughout the entire process.

Doctors face numerous challenges, including: patient health risks, potential medical malpractice liability, frantic calls from the operating room staff prior to surgery because of a scheduling mishap, and a waste of time and energy on cases that are moved or cancelled without notification.

Healthcare providers also face their own share of challenges associated with or directly impacting scheduling, such as: more services needed by patients, there are now more (and much older) patients to serve and liability for negligence caused by staff at the facility.

There is therefore a need for methods and/or systems that can prevent scheduling errors. There is also a need for systems and methods that enhance the overall scheduling process so that errors can be reduced or altogether avoided.

SUMMARY OF THE INVENTION

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

In accordance with a feature of the present invention, an operating platform is provided that enables physicians, such as surgeons, to schedule medical procedures (e.g., surgeries) in coordination with medical facilities (e.g., operating rooms at hospitals) and third party service and equipment suppliers (e.g., medical equipment distributors).

In accordance with another feature of the present invention, medical equipment distributors can more accurately and timely provide their customers/surgeons with implants that might be needed for surgical cases scheduled using aspects of the present invention.

In accordance with another feature of the present invention, hospitals and necessary support personnel can all be accurately notified and scheduled for a medical case with a reduction in error using aspects of the present invention.

In accordance with another feature of the present invention, data associated with medical case scheduling can be archived in compliance with HIPAA requirements and generic information (e.g., statistics) can be extracted from the data for use by medical service and equipment providers, insurance companies and various third parties of interest for use in business, demographical and socioeconomic studies, and for educational purposes.

Systems and methods are described that can enable the scheduling and tracking of surgical cases over the internet using graphical user interfaces accessible to medical personnel (e.g., surgeons) and logistics suppliers (e.g., facilities and equipment suppliers). For example, the present invention can assist a surgeon or the surgeon's scheduler to reduce problems typically encountered with or after scheduling and coordinating surgical cases in the past.

Surgical case scheduling users can be provided an online software solution that enables them to enter all pertinent information for a medical case into an online order form. The user can select the people that need to be contacted using a graphical user interface and completes scheduling by selecting and enter or "connect" button on the interface. After selections are made by the scheduler, the system can enable each person indicated by the scheduler to be automatically notified electronically over a data network about the case (e.g., via e-mail). Electronic notifications (e.g., acceptance, rejections and conflict indications) are returned from each person (e.g., vendors, medical personnel, medical facility/hospital). The system can enable the archiving of medical/surgical cases scheduled using the system. The data can be made available to medical consultants. Consultants can be provided access to the archived data electronically. Data can be provided to industry (including consultants) for a fee. Archived data can provide interested parties accurate data based on actual procedures. Data can also be used to help the manufacture produce better products based on user input.

There are several benefits provided to medical practitioners by the present invention. Office overhead can be reduced because what used to take hours to accomplish now takes minutes. Schedulers are freed up to do other beneficial services around the office. Scheduling errors are virtually eliminated. Surgeons can optionally work with one highly experienced consultant using the present invention, instead of having to work with multiple sales representatives using manual systems. In an automated system, consultants can be the point person. Consultants can provide surgeons with expert advice on all current and available implant systems available in the marketplace. Consultants can provide pre-operative and intra-operative back up plans if a patient's anatomy is challenging. Consultants can always check with a surgeons preferred implant vendor the night before each case to verify that everything is ready. Surgeon/hospital Operating Room (OR) time can be streamlined because everything that was ordered by the surgeon is present. Consultants can match surgeons with companies looking to conduct research.

Medical facilities also benefit from use of the present invention. One point person can be established for the scheduled procedure. Precision can be achieved over equipment delivery from distributors for every case. Surgeons can use the system to more effectively schedule procedures and consolidate cases. Efficiency in case scheduling decreases overall operating costs because there is less waste of personnel time and resources when medical procedures are accurately scheduled and all parties are on the same page. Saving can be achieved with substantially less facility (e.g., operating room) idle time between scheduled procedures.

Medical equipment distributors also benefit from the invention because less time is wasted following up with parties to avoid inaccurate scheduling and/or equipment requests.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

FIGS. 7-12 illustrate electronic forms, which can also be represented as screen shots on a computer user interface utilized by the scheduler, in accordance with an exemplary medical case scheduling session by a scheduler.

FIGS. 13-19 illustrate electronic notices that can be transmitted by the scheduling system for receipt by parties identified during the scheduling process as requiring notification.

DETAILED DESCRIPTION

The particular values and configurations discussed in these non-limiting examples can be varied and are cited merely to illustrate at least one embodiment and are not intended to limit the scope thereof.

What is described herein are systems and methods that enable the scheduling and tracking of surgical cases over the internet using graphical user interfaces accessible to surgeons and logistics suppliers (both medical and support). The invention will also archive data in compliance with HIPAA requirements that will enable medical device manufacturing companies to learn information on surgical statistics, studies and feedback on their products.

Figure 1:
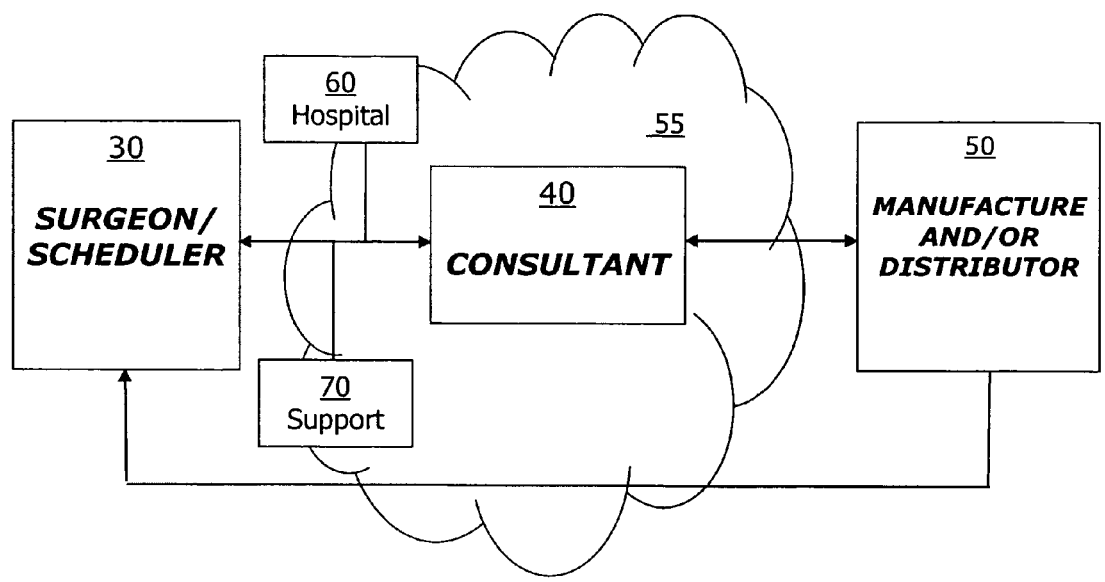
FIG. 1 illustrates an operating platform which, in accordance with the present invention, can enable medical procedure schedulers to successfully schedule medical procedures, enable equipment providers to accurately and timely provide equipment (e.g., surgeons with implants that are needed for each surgical case), and hospitals and necessary support personnel with requests/notice to be available and all be on the same page for a scheduled medical procedure.
Figure 2:
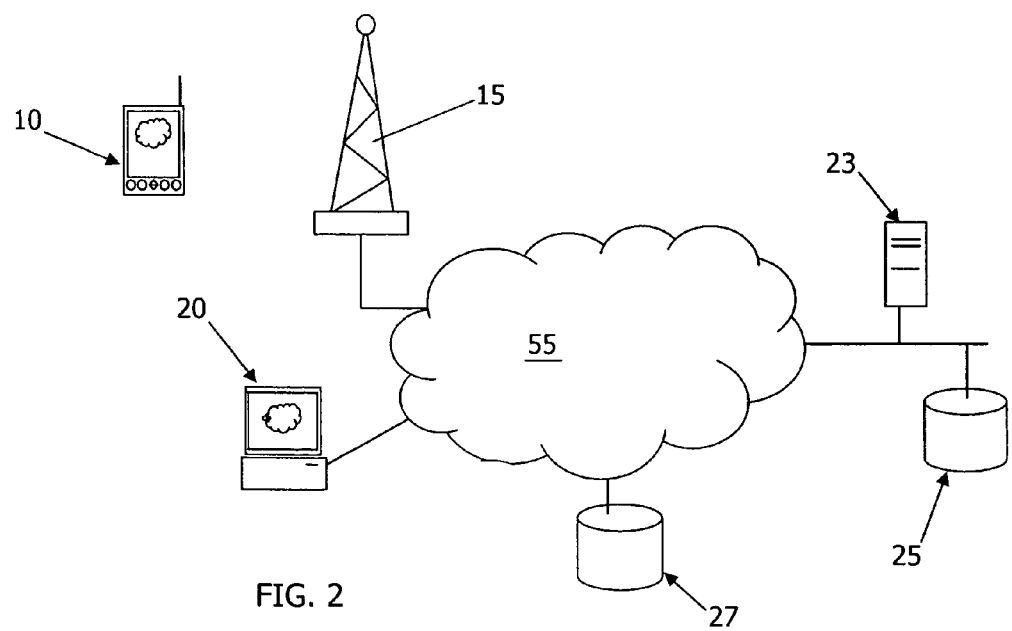
FIG. 2 illustrates a system architecture including hardware that can be used to successfully implement a medical case scheduling and associated data management system.

Referring to FIGS. 1 and 2, networked, interacting components of a medical case scheduling and associated data management system are illustrated. FIG. 1 represents an operating platform which will enable schedulers for medical providers (e.g., surgeons or schedulers operating on the surgeon's behalf) to successfully schedule medical procedures (e.g., surgeries), enable equipment distributors to accurately and timely provide the medical equipment (e.g., surgeons with implants that are needed for each surgical case), and medical facilities such as hospitals and necessary support personnel to be available and all be on the same page for a scheduled medical procedure. FIG. 2 illustrates a system architecture including hardware that can be used to successfully implement a medical case scheduling and associated data management system.

As shown in FIG. 1, planning and interaction can generally occur through a data network 55 between representatives of: a surgeon/scheduler 30, consultants 40, manufacturers/distributors 50, hospital staff 60 and support personnel 70. These parties are typically responsible for ensuring that a medical procedure such as a surgical case is ready to go within a medical facility, such as hospital operating room facilities, and will include the proper medical support personnel and equipment distributors. Hospital facilities 60 and support personnel 70 are important, traditional aspects of the scheduling process, but have not been automated as described herein. Consultants 40 and/or distributors 50 can be included as an important component of the automated scheduling process to ensure complete, accurate medical case scheduling is accomplished by all relevant entities.

Referring to FIG. 2, a system architecture is illustrated of hardware that can be used to successfully implement a medical case scheduling and associated data management system. A surgeon, scheduler, consultant, distributor, hospital, and medical support personnel can communicate with the medical case scheduling and associated data management system using office computers 20 and/or wireless communication devices 10 and associated communications hardware 15 over an electronic data network 55. The data network 55 facilitates the transfer of scheduling and management processes between users. A combination of servers 23 and databases 25 and 27 can be used in the system to maintaining records and facilitate the scheduling and data management processes. The scheduling system can be carried out with a computer having online access to a remote scheduling server including scheduling software, or can include the use of a local computer having network access to a remote scheduling server but having the scheduling software, including modules loaded onto the local computer for enabling a scheduler to log into the scheduling system, enter scheduling data into the scheduling system, and connect with parties to provide data to parties through the system including sending/receiving notifications to/from the system.

Medical cases all begin with a surgeon-patient examination. A surgeon/scheduler then books a surgical case for the patient. In most offices, the surgeon typically fills out a scheduling form (e.g., data sheet) while the patient is present. The surgeon might then gives this data sheet to his scheduler and the scheduler does the scheduling by notifying all parties required for a case. Notification typically occurred telephonically or via email. What occurs following the physical collection of data by the surgeon and/or the creation of the sheet can be automated in accordance with features of the present invention.

Figure 3:
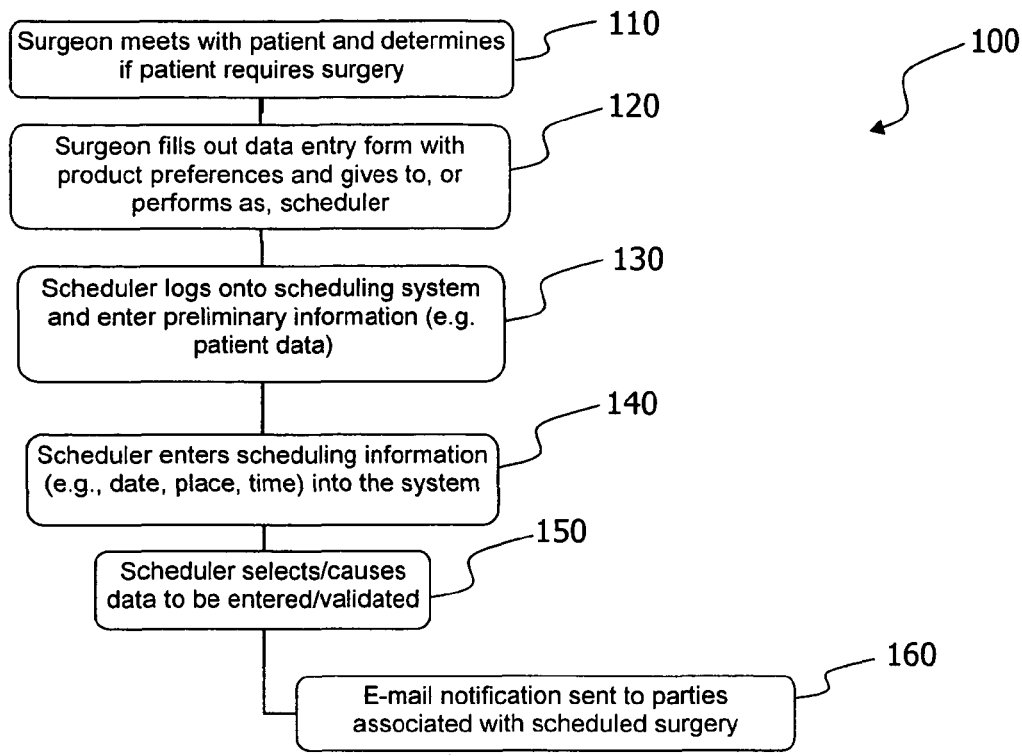
FIG. 3 illustrates a flow diagram of steps can be carried out to schedule a medical procedure.

Referring to flow diagram 100 illustrated in FIG. 3, certain steps can be carried out to schedule a medical procedures (e.g., surgical case). This example is for a surgery, although others medical procedures can be assumed as well). As shown in Step 110, the surgeon first consults with a patient and determines whether surgery is necessary. As shown in Step 120, the surgeon fills out a scheduling form (typically paper-based) and gives the filled out form to a staff person who will perform as a scheduler. It should be appreciated that the surgeon can also be the scheduler and perform scheduling tasks as indicated in Step 120. It should also be appreciated that data can be entered into a system directly, using user interfaces that are typically associated with networked computers, without the need to fill out a form.

As shown in Step 130, the scheduler/surgeon logs onto a scheduling system and enters information necessary to successfully schedule the case. It is important that the scheduler enters all pertinent information regarding the surgical case and that is minimally necessary to accomplish scheduling of a case. For example, the scheduler can enter the patient information, insurance info, ICD-9 codes, CPT-4 codes and identify all the equipment needed for the case. Needed equipment can include, for example: implants, a particular OR table/ room and a C-arm if needed. The scheduler can also enter other data into the system such as requests for a particular consultant, monitoring or Durable Medical Equipment (DME).

Information entered by the scheduler can be broken into two categories: Preliminary information and scheduling information. Preliminary information (or "Patient data") provided by the scheduler can include patient identifying data insurance data, CPT-4 and ICD-9 codes, etc. As shown in Step 140, the scheduler can use the system to select surgical event information including a surgery date, hospital, equipment (e.g., medical prosthetics), and support personnel. As shown is Step 150, the scheduler can cause the entered data to be validated by the scheduling system. Validation can simply include automatic confirmation by the system that all required data has been entered. If the data is acceptable, the system will send out electronic confirmations as shown in Step 160. For example, emails can be sent to: surgeon, hospital, anesthesia, cell saver, bracing, spinal cord monitoring and anyone pertinent to the surgical case. If the data is not acceptable (i.e., due to inaccurate data entry, scheduling conflicts and/or equipment shortage), the scheduler will be required to repeat step 140.

Figure 4:
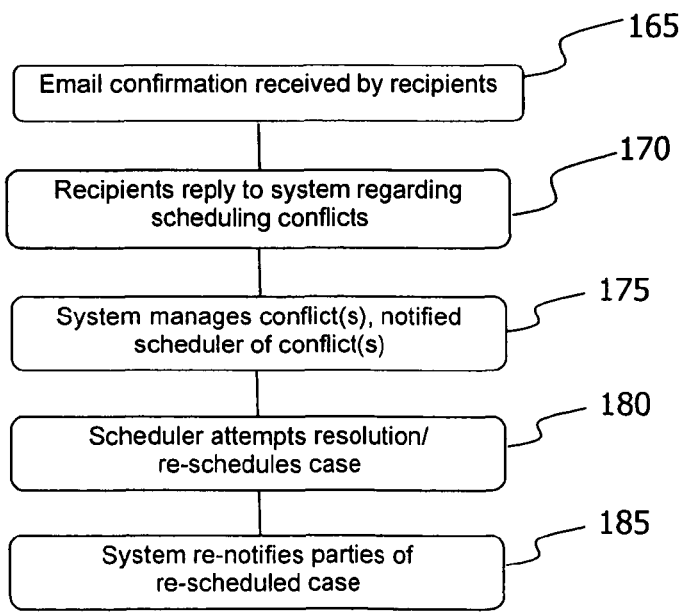
FIG. 4 illustrates a flow diagram of steps recipients of electronic notification can carry out to reply to the system indicating a conflict with a proposed schedule.

It should be appreciated that the system can accept the data entered in Step 140 following user action at Step 150 without validation as shown in Step 160. In such a case, electronic notifications (e.g., email) would be sent out to the parties confirming the scheduled case immediately following step 150. As shown in FIG. 4, after confirmation is received by recipients as shown in Step 165, the recipient parties of email notification can reply to the system indicating a conflict with the schedule as shown in Step 170. As shown in Step 175, the system can manage notification of the scheduling conflict for all parties. If a conflict is determined to exist by the system, the system can notify the scheduler who can then resolve the conflict by attempting to reschedule the case as shown in Step 180. Once rescheduled, the system will re-notify all parties of the rescheduled case via email as shown in Step 185. It should be appreciated that notification of a rescheduled case may only include a change in at least one of the parameters necessary to fulfill a case (i.e., a change of at least one of: surgery time and date, hospital, support staff, equipment, etc.).

Figure 5:
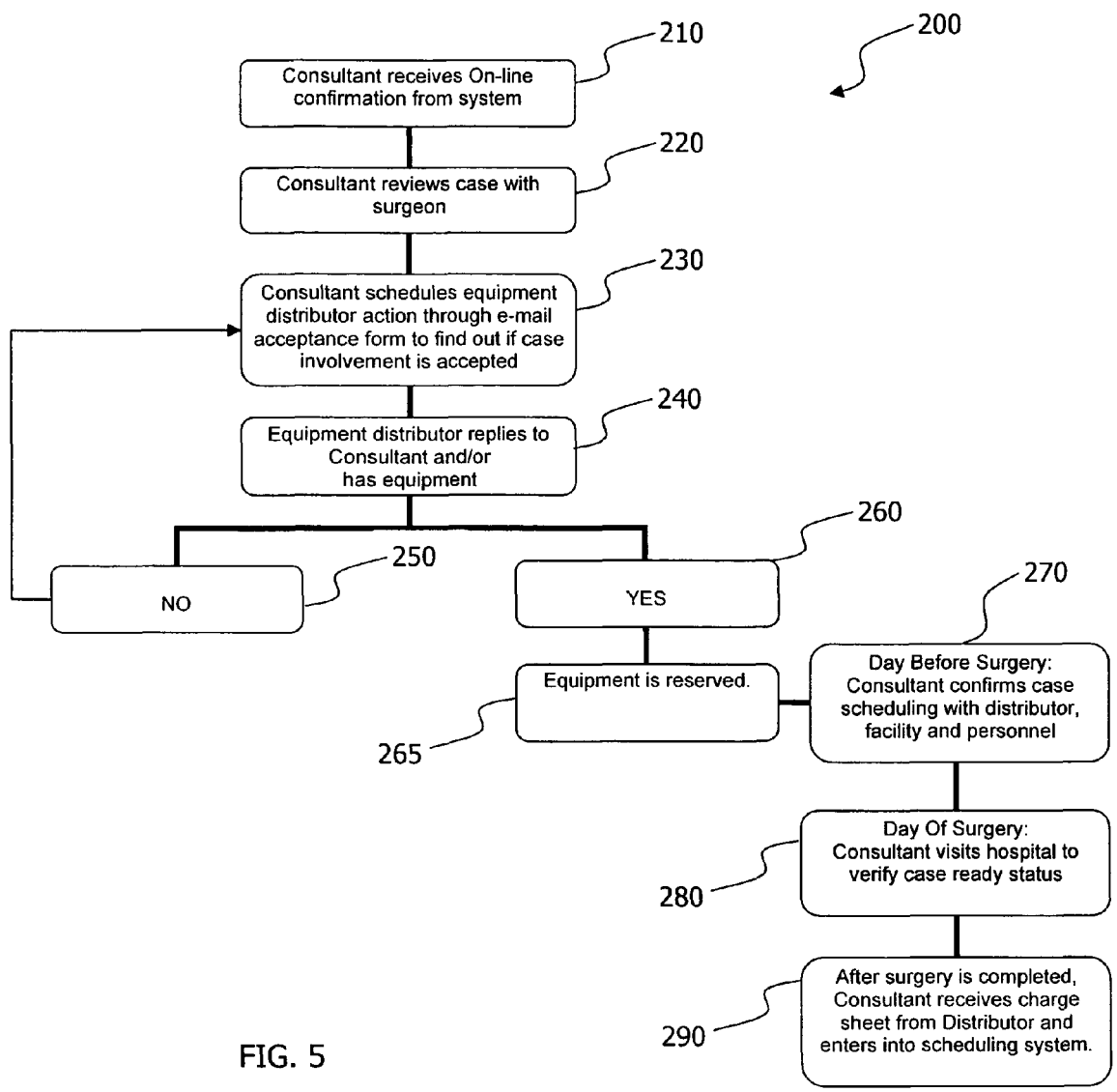
FIG. 5 illustrates a flow diagram of depicting optional actions that can be carried out by a consultant when used by a surgeon in a case.

Referring to FIG. 5, a flow diagram 200 depicting optional actions that can be carried out by a Consultant when used by a surgeon in a case is illustrated. As shown in Step 210, a consultant receives an on-line confirmation from the system (scheduler). As shown in Step 220, the Consultant can review the scheduled case with the surgeon (or the surgeon's staff). As shown in Step 230, the Consultant can schedule equipment with the vendor of choice of the surgeon. The distributor is notified (e.g., orders) through e-mail acceptance form to find out if the distributor accepts involvement in the case. As shown in Step 240, the equipment distributor replies to the consultant and can confirm equipment availability. If equipment is not available from the distributor as shown in block 250, the consultant can find another distributor or equipment source as shown by the flow diagram's return to step 230. If the equipment is available as show in Step 260, equipment is reserved as shown in Step 265.

As shown in step 270, the consultant can be used to confirm scheduling with the equipment distributor, hospital, and support personnel one day before the surgery is scheduled. On the day of surgery, the consultant can visit the hospital and make sure that the case is ready as shown in Step 280. After a surgery is completed, the consultant can receives a charge sheet from the distributor and enters it into the scheduling system for billing as shown in Step 290.

Figure 6:
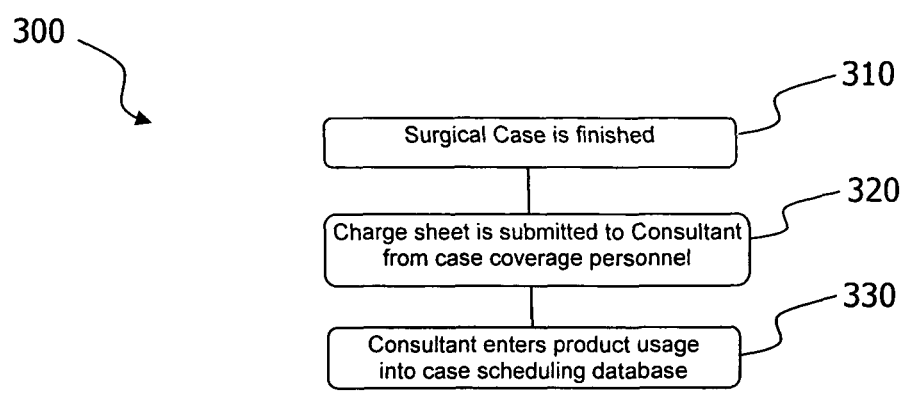
FIG. 6 illustrates a flow diagram of how post surgery data can be handled.

Referring to FIG. 6, a flow diagram 300 illustrating post surgery data handling is shown. As shown in Step 310, a surgical case comes to completion. In Step 320, a charge sheet can be submitted to the hospital and consultant from case coverage personnel. The consultant enters the product usage information into the case scheduling database as shown in Step 330, wherein the data can be kept for future retrieval and used by the surgeon and interested third parties.

FIGS. 7-12 illustrate electronic forms, which can also be represented as screen shots on a computer utilized by the scheduler, in accordance with an exemplary medical case scheduling session by "Barb" the scheduler. Referring to FIG. 7, the scheduler enters the scheduling system and is greeted on the graphical user interface by a "Welcome" page whereon the scheduler is asked to sign in. Surgeons will have a way to control access to their accounts. If scheduler terminates employment with a surgeon, a surgeon will be able to prevent access to the scheduling system by the terminated employee so that patient data is protected. Once the scheduler is signed in and authenticated, the scheduler can begin entering patient information into the system as shown in FIG. 8. The patient information can be what was referred to above as "preliminary information". After the patient information is entered, the scheduler can enter "scheduling" data into the system as shown in FIG. 9.

Enough information to schedule a surgical case has been entered up to FIG. 9; however, it can be appreciated that additional information related to equipment, such as prosthetics, can be a useful component of scheduling a surgery. As shown in FIG. 10, the scheduler can also optionally choose equipment needed for the type of surgery identified in FIG. 9. The "Back" button in FIG. 10 will enable the scheduler to return to the previous scheduling page to make corrections (e.g., in case equipment options are incorrect based on the type of surgery entered). Once the equipment is chosen it can be submitted to the system using the "Submit" button on the form represented by FIG. 10. The scheduler can be directed to another equipment-related page, as shown in FIG. 11, wherein additional categories or information related to the equipment chosen on Page 10 can be entered. Again, the "Back" and "Submit" buttons can be selected by the scheduler following data entry. FIG. 12 illustrates the last page that the scheduler will encounter during the scheduling of a surgical case. In FIG. 12, the scheduler will identify the parties that should be electronically notified of the scheduled case. Where a Consultant is used, the scheduler can also identify parties that the Consultant can contact on the schedulers behalf (typically manufacturers or distributors of equipment). Once all the parties requiring notification have been identified by the scheduler, the scheduler can complete the process of scheduling the case by selecting the "Case Connect" button on the graphical user interface. Once the data is submitted to the scheduling system, the parties will be notified. Notification can occur after the system has validated the data as discussed above with respect to FIG. 3, or immediately after entry the by scheduler as discussed with respect to FIG. 4.

FIGS. 13-19 illustrate electronic notices that can be transmitted by the system for receipt by parties identified during the scheduling process as requiring notification. Once official entry of the data is selected, all the information is routed to the appropriate entities (e.g., hospital, doctor, profusion, SSEP monitoring and anyone else that needs the information). Scheduling information can be received via e-mail. FIGS. 13-18 illustrates examples of letters that would go to surgeons, hospitals, support personnel and equipment providers. FIG. 19 illustrates an example of a letter than can be sent or electronically transmitted to the patient and provides the patient with, inter alia, scheduled case information, pre-operative requirements (e.g., "do not eat after midnight . . . ") and point of contact information.

Optionally, a Consultant (and as discussed above) responsible for supplying equipment can also be emailed. Following notification, the Consultant can work on ensuring that all necessary equipment is made available for the scheduled case. The Consultant can be designated as the agent of record for the surgeon's scheduled surgical cases. The Consultant can call or email the Equipment Vendors that have been requested by the surgeon. The case can be available online with limited information for the manufacture and they will need to decide if they want the case. Because the Consultant can be designated as the agent of record with the surgeon, the Equipment Vendors can be required to accept an online agreement of terms and conditions including an agreement to pay the Consultant a case referral fee. Once the Equipment Vendor clicks to accept the terms and conditions of the case, specific case information can be revealed. If the Equipment Vendor has what the surgeon needs, it can be ordered by the Consultant. If the Equipment Vendor does not have the equipment (e.g., a set or enough implants) to accomplish the surgery, the Consultant can call another Equipment Vendor as a back up. It can be left up to the Consultant working on behalf of the surgeon to be sure everything is ready for each case.

Equipment vendors generally deliver the implants to the hospital. On the day of surgery, the equipment vendor can appoint a case coverage representative to cover and break down the equipment after the case. Consultants, when used, generally should not and probably will not deliver equipment, or cover the case and break down the case. It is typically, and can be made, the sole responsibility of the equipment vendors to provide these services.

As can be appreciated from the methods steps outlined above, the scheduling system can be a tremendous asset to surgeons. In accordance with a method of doing business, a scheduling system vendor can license surgeons to use the system for no charge in exchange for the surgeons' use of the system and vendor consulting services. The consultant can train the office staff and the surgeon on how to enter the cases into the system and can consult with third party vendors that need to be kept abreast of the case for supply purposes.

In addition, the consultant can offer the surgeon various opportunities to become involved with companies that are looking to conduct research thru pre and post marketing studies. Consultants can also facilitate any 510K or possible IDE studies that companies are generally interested in.

The scheduling system and methods described herein can enable surgeons to run a much better operation and they will have the ability to get real-time information regarding their schedules and surgical cases. The system can enable surgeons to use the scheduling system to search for past surgeries or implants used by searching the date, hospital, patient name or the ICD-9 codes. This can allow a surgeon to respond better to patients that may need revision surgery. The surgeons and their schedulers can log onto the scheduling system anywhere there is an internet connection.

Surgeons will own their patient data and vendors might be able to own the demographic data. Surgeons should be able to take their information with them if they changed practices or employment. It is important that data goes with the surgeon that conducted the surgery. Patient data that is entered into the system should generally belong to the surgeon and if the surgeon were to leave their practice, the data can easily follow the surgeon given the architecture of the present system. The demographic data that is collected, however, can remain the property of the scheduling system vendor and can be compiled in a searchable database for statistical and other future uses that do not violate privacy laws, or HIPAA.

Data maintained by surgeons in a database can be searchable. A surgeon can find information about a patient or surgeries conducted in the past by looking up that patient's name or the surgery type. Other information can be researched as well in a searchable database. Such information can be helpful to medical practice. Surgeons often store paper files yet do not have easy access to them. Surgeon Reports for different types of surgery (like how many anterior cervical cases has the surgeon done in the past 6 months or at a particular hospital) can be very valuable information to the surgeon. This type of information can also be valuable to equipment suppliers, service providers, insurance companies, etc. The system can store information by demographic group (city, state, sex, age group . . . ) without breaching privacy.

It will now be appreciated following the above-disclosed embodiments and other features and functions, or alternatives, thereof, that variations of the disclosed invention may be desirably combined into many other different systems of applications. Also that various presently unforeseen or unanticipated alternatives, modifications, variations or improvements therein maybe subsequently made by those skilled in the art which are also intended to be encompassed by the following claims.

What is claimed is:

1. A method for reducing surgical scheduling conflicts and errors, said method comprising:
   a surgical case scheduler logging into an electronically networked medical scheduling system for a surgeon to schedule a first surgical case request comprising a medical procedure in coordination with an operating room at a medical facility, a medical equipment distributor, and an equipment supplier or vendor;
   said surgical case scheduler entering preliminary patient data together with at least one of, case date, case place, case time, surgical procedure, required equipment, requested medical personnel, medical distributors, and medical supplies into said electronically networked medical scheduling system as part of said first surgical case request;
   storing said first surgical case request in a database associated with said electronically networked medical scheduling system;
   electronically notifying a plurality of surgical case scheduling information recipients to said first surgical case wherein surgical case scheduling information recipients represent entities required to process said surgical procedure included in said first surgical case request wherein said plurality of surgical case scheduling information recipients include a party representing a hospital, a party representing said medical equipment distributor, and a party representing medical personnel;
   automatically sending electronic notifications to said surgical case scheduling information recipients when a conflict exists with said scheduled said first surgical request;
   archiving data associated with said first surgical case request and extracting statistical information and using said archived data for business, demographical, and socioeconomic studies, and for educational purposes by medical service and equipment providers, insurance companies and various third parties of interest;
   matching said surgeon with a research company; and
   conducting marketing research between said surgeon and said research company based on said archived data.

2. The method of claim 1 wherein electronic responses are received by said surgical case scheduler from at least one surgical case scheduling information recipients accepting a first surgical case request.

3. The method of claim 1 wherein an electronic response is received by said surgical case scheduler from at least one surgical case scheduling information recipients indicating a conflict with a first surgical case request.

4. The method of claim 3 further comprising:
   entering a second surgical case request into an electronically networked medical scheduling system, said second surgical case request including patient data and changes to at least one of: the case date, the case place, the case time, the required equipment, the requested medical personnel, and wherein said surgical case scheduler causes said second surgical case request to be accepted into said electronically networked medical scheduling system.

5. The method of claim 4 further comprising:
   sending electronic notifications of said second surgical case request to a surgical case scheduling information recipients;
   receiving electronic responses from said surgical case scheduling information recipients; and
   at least one said scheduling information recipients accepting said second surgical case request.

6. A method for reducing surgical scheduling conflicts and errors, said method comprising:
   a surgeon logging into a networked medical procedure scheduling system to electronically schedule a first surgical request medical procedure in coordination with an operating room at a medical facility, a medical equipment distributor, and an equipment supplier or vendor;
   entering preliminary patient data together with at least one of: medical procedure date, medical procedure place, medical procedure time, required equipment, requested medical personnel, medical distributors, and medical supplies as part of said first medical procedure request;
   storing said first medical procedure request in a database associated with said networked medical procedure scheduling system;
   said networked medical procedure scheduling system automatically sending an electronic notification about said first medical procedure request to a medical procedure scheduling information recipients, said medical case scheduling information recipients representing an entity required to process said first medical procedure and including at least one party representing at least one of: a medical facility, medical personnel, and equipment distribution;
   said networked medical procedure scheduling system automatically sending electronic notifications to said surgical case scheduling information recipients when a conflict exists with said scheduled said first surgical request;

said networked medical procedure scheduling system archiving data associated with said first surgical case request and extracting statistical information and said networked medical procedure scheduling system using said archived data for business, demographical, and socioeconomic studies, and for educational purposes by medical service and equipment providers, insurance companies and various third parties of interest;

said networked medical procedure scheduling system matching said surgeon with a research company; and said networked medical procedure scheduling system conducting marketing research between said surgeon and said research company based on said archived data.

7. The method of claim 6 wherein said surgical case scheduler receives an electronic response from said surgical case scheduling information recipients accepting said first medical procedure request.

8. The method of claim 6 wherein said surgical case scheduler receives an electronic response from at least one of said surgical case scheduling information recipients indicating a conflict with said first surgical case request.

9. The method of claim 8 further comprising:
said surgical case scheduler electronically submitting a second surgical case request through said medical procedure scheduling system, said second surgical case request including patient data and changes to at least one of: procedure date, procedure place, procedure time, required equipment, requested medical personnel, and wherein said surgical case scheduler causes said second surgical case request to be electronically accepted into said networked medical procedure scheduling system.

10. The method of claim 9 further comprising:
said medical procedure scheduling system sending electronic notifications of said second medical procedure request to said surgical case scheduling information recipients; and
said surgical case scheduler receiving electronic responses from said surgical case scheduling information recipients accepting said second medical procedure request.

11. The method of claim 9 further comprising:
said medical procedure scheduling system sending electronic notifications of said second medical procedure request to said surgical case scheduling information recipients, said medical procedure scheduling information recipients including at least one new party associated with: a medical facility, medical personnel, equipment distribution; and
said surgical case scheduler receiving electronic responses from said surgical case scheduling information recipients accepting said second medical procedure request.

12. A medical procedure scheduling system for reducing surgical scheduling conflicts and errors, comprising:

a user interface through which medical procedure schedulers access a medical procedure scheduling system, said system comprising a processor, a data bus coupled to said processor, and a computer-usable tangible storage device storing computer program modules for a surgeon to schedule a first surgical request medical procedure in coordination with an operating room at a medical facility, a medical equipment distributor, and an equipment supplier or vendor, said computer program modules comprising program instructions executable by said processor, said computer program modules comprising:

a scheduling module that accepts a plurality of medical procedure requests, said medical procedure requests including patient data and least one of: procedure date, procedure place, procedure time, required equipment, requested medical personnel, medical distributors, and medical supplies;

a storage module for storing said medical procedure requests in a database and archiving data associated with said first surgical case request and extracting statistical information and said networked medical procedure scheduling system using said archived data for business, demographical, and socioeconomic studies, and for educational purposes for use by medical service and equipment providers, insurance companies and various third parties of interest, wherein said medical procedure scheduling system matches said surgeon with a research company and conducts marketing research between said surgeon and said research company based on said archived data; and a connection module that sends electronic notifications of said medical procedure requests over an electronic data network to parties representing a medical facility, medical personnel and medical equipment distributors and to parties when a conflict exists with said scheduled said first surgical request.

13. The system of claim 12 wherein said connection module receives electronic notifications on behalf of medical procedure schedulers from parties accepting medical procedure requests.

14. The system of claim 12 wherein said connection module receives electronic notifications on behalf of medical procedure schedulers from parties declining medical procedure requests.

15. The system of claim 12 wherein said connection module receives electronic notifications on behalf of medical procedure schedulers from parties indicating a conflict with medical procedure requests.

16. The method of claim 1 wherein said surgical case scheduler includes a surgeon or a surgeon's representative.

* * * * *